(12) United States Patent
Copes

(10) Patent No.: US 6,960,706 B2
(45) Date of Patent: Nov. 1, 2005

(54) INBRED CANTALOUPE LINE 442

(75) Inventor: Bill Copes, Sacramento, CA (US)

(73) Assignee: Harris Moran Seed Company, Modesto, CA (US)

( * ) Notice: Subject to any disclaimer, the term of this patent is extended or adjusted under 35 U.S.C. 154(b) by 114 days.

(21) Appl. No.: 10/091,534

(22) Filed: Mar. 7, 2002

(65) Prior Publication Data

US 2003/0177539 A1 Sep. 18, 2003

(51) Int. Cl.$^7$ ............................ A01H 5/00; A01H 5/10; A01H 1/00; C12N 15/82; C12N 5/04
(52) U.S. Cl. ................ 800/309; 800/260; 800/278; 800/279; 800/300; 800/301; 800/302; 800/303; 435/410
(58) Field of Search ................................ 800/260, 309, 800/278, 279, 300, 301, 302, 303, 265; 435/410, 430

(56) References Cited

U.S. PATENT DOCUMENTS

| | | | |
|---|---|---|---|
| 5,777,196 A | 7/1998 | Hall | |
| 5,948,957 A | 9/1999 | Chapko et al. | |
| 5,969,212 A | 10/1999 | Getschman | |
| 6,420,631 B1 * | 7/2002 | Copes | 800/309 |

OTHER PUBLICATIONS

Riley et al, 2001, J. Entomological Sci. 36:46–56.*
Adelberg, Jeffrey W., et al., 1994, Explant Origin Affects the Frequency of Tetraploid Plants from Tissue Cultures of Melon, HortScience, vol. 29(6), pp. 689–692.
Bennetzen, Jeffrey L., et al., 1992, Approaches and Progress in the Molecular Cloning of Plant Disease Resistance Genes, Genetic Engineering, vol. 14, pp. 99–124.
DeBolle, Miguel F.C., et al., 1996, Antimicrobial Peptides from *Mirabilis jalapa and Amaranthus caudatus*: Expression, Processing, Localization and Biological Activity in Transgenic Tobacco, Plant Molecular Biology, vol. 31, pp. 993–1008.
Ezura, Hiroshi, et al., 1994, Ploidy of Somatic Embryos and the Ability to Regenerate Plantlets in Melon (*Cucumis melo* L.), Plant Cell Reports, vol. 14, pp. 107–111.
Ezura, Hiroshi, et al., 1995, Selection of Somaclonal Variants with Low–temperature Germinability in Melon (*Cucumis melo* L.), Plant Cell Reports, vol. 14, pp. 684–688.
Pang, Sheng–Zhi, et al., 1992, Expression of a Gene Encoding a Scorpion insectotoxin Peptide in Yeast, Bacterial and Plants, Gene, vol. 116, pp. 165–172.
Zhang, X.P., et al., 1996, Development of Genic Male–sterile Watermelon Lines with Delayed–green Seedling Marker, HortScience, vol. 31(1), pp. 123–126.

* cited by examiner

*Primary Examiner*—Anne Kubelik
(74) *Attorney, Agent, or Firm*—Jondle & Associates P.C.

(57) ABSTRACT

An inbred cantaloupe line, designated 442, is disclosed. The invention relates to the seeds of inbred cantaloupe line 442, to the plants of inbred cantaloupe line 442 and to methods for producing a cantaloupe plant, either inbred or hybrid, by crossing the inbred line 442 with itself or another cantaloupe line. The invention further relates to methods for producing a cantaloupe plant containing in its genetic material one or more transgenes and to the transgenic plants produced by that method and to methods for producing other inbred cantaloupe lines derived from the inbred 442.

27 Claims, No Drawings

INBRED CANTALOUPE LINE 442

BACKGROUND OF THE INVENTION

The present invention relates to a new and distinctive cantaloupe inbred line, designated Inbred 442. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, fruit and agronomic quality such as sugar levels, small cavity size, flesh color or texture, rind firmness or strong net, resistance to diseases and insects, and tolerance to drought and heat.

Practically speaking, all cultivated forms of cantaloupe belong to the highly polymorphic species *Cucumis melo* L. that is grown for its sweet edible fruit. The term cantaloupe, as used herein, refers to the American usage of the term which is used to describe the netted melons commonly referred to as cantaloupe or muskmelon in U.S. commerce. As a crop, cantaloupes are grown commercially wherever environmental conditions permit the production of an economically viable yield. They are produced on non-climbing vines that are prostrate on the soil. On healthy plants there is a canopy of large, soft, hairy leaves, generally heart shaped and somewhat lobed. Fruits may be orange fleshed or green fleshed. The fruit surface is generally netted and roughened and in some varieties sutured. Fruit shape is generally round to oval and ranges in size from five to eight inches long and about equal in diameter. In the United States, the principal fresh market cantaloupe growing regions are California, Arizona and Texas which produce approximately corner 96,000 acres out of a total annual acreage of more than 113,000 acres (USDA, 1998). Fresh cantaloupes are available in the United States year-round although the greatest supply is from June through October. Fresh cantaloupes are consumed in many forms. They are eaten sliced or diced and used as an ingredient in many prepared foods.

*Cucumis melo* is a member of the family Cucurbitaceae. The Cucurbitaceae is a family of about 90 genera and 700 to 760 species, mostly of the tropics. The family includes pumpkins, squashes, gourds, watermelon, loofah and several weeds. The genus *Cucumis*, to which the cantaloupe, cucumbers, and several melons belong, includes about 70 species. *Cucumis melo* includes a wide range of cultivated plants. Although crosses outside the species are sterile, intraspecific crosses are generally fertile, resulting in a confusing range of variation. The more common cultivated plants fall into four main groups. First are the true cantaloupes of Europe. These have thick, scaly, rough, often deeply grooved, but not netted rinds. Second are the muskmelons, mostly grown in the United States, where they are incorrectly called cantaloupes. These have finely netted rinds with shallow ribs. Third are the casaba or winter melons with large fruits. These have smooth, often yellow rinds. The honeydew melons are in this third group. Fourth are a group of elongated melons of India, China and Japan which are grown as vegetables. Other classification schemes and peculiar cultivars could be presented.

Cantaloupe is a simple diploid species with twelve pairs of highly differentiated chromosomes. Large field spaces are required for cantaloupe and the need for labor intensive hand pollination for selfing as well as cross pollination has resulted in a lag in the knowledge of cantaloupe genetics relative to such crops as tomato. Cantaloupe flowers open after sunrise; the exact time depends on environmental conditions such as sunlight, temperature and humidity. The flower closes permanently in the afternoon of the same day. Almost all pollen is collected and transferred before noon. Typically flowers are staminate although some are also hermaphroditic. Although hermaphroditic flowers are self-fertile, they are incapable of performing self-pollination. Insects are required for pollination. The primary pollinators are bees, particularly honey bees.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior cantaloupe inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same cantaloupe traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new cantaloupe inbred line.

The development of commercial cantaloupe hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., "Principles of Plant Breeding" John Wiley and Son, pp. 115–161, 1960; Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny.

Cantaloupe is an important and valuable field crop. Thus, a continuing goal of plant breeders is to develop stable, high yielding cantaloupe hybrids that are agronomically sound. The reasons for this goal are obviously to maximize the amount of fruit produced on the land used as well as to improve the fruit agronomic qualities. To accomplish this goal, the cantaloupe breeder must select and develop cantaloupe plants that have the traits that result in superior parental lines for producing hybrids.

SUMMARY OF THE INVENTION

According to the invention, there is provided a novel inbred cantaloupe line, designated Inbred 442. This invention thus relates to the seeds of inbred cantaloupe line 442, to the plants of inbred cantaloupe line 442 and to methods for producing a cantaloupe plant produced by crossing the inbred line 442 with itself or another cantaloupe line, and to methods for producing a cantaloupe plant containing in its genetic material one or more transgenes and to the transgenic cantaloupe plants produced by that method. This invention also relates to methods for producing other inbred cantaloupe lines derived from inbred cantaloupe line 442 and to the inbred cantaloupe lines derived by the use of those methods. This invention further relates to hybrid cantaloupe seeds and plants produced by crossing the inbred line 442 with another cantaloupe line.

The cantaloupe plant of the invention may further comprise, or have, a cytoplasmic factor or other factor that is capable of conferring male sterility. Parts of the cantaloupe plant of the present invention are also provided, such as e.g., pollen obtained from an inbred plant and an ovule of the inbred plant.

In another aspect, the present invention provides regenerable cells for use in tissue culture or inbred cantaloupe plant 442. The tissue culture will preferably be capable of regenerating plants having the physiological and morphological characteristics of the foregoing inbred cantaloupe plant, and of regenerating plants having substantially the same genotype as the foregoing inbred cantaloupe plant. Preferably, the regenerable cells in such tissue cultures will be embryos, protoplasts, meristematic cells, callus, pollen, leaves, anthers, stems, petioles, roots, root tips, or flowers or the like. Still further, the present invention provides cantaloupe plants regenerated from the tissue cultures of the invention.

Another objective of the invention is to provide methods for producing other inbred cantaloupe plants derived from inbred cantaloupe line 442. Inbred cantaloupe lines derived by the use of those methods are also part of the invention.

The invention also relates to methods for producing a cantaloupe plant containing in its genetic material one or more transgenes and to the transgenic cantaloupe plant produced by that method.

In another aspect, the present invention provides for single gene converted plants of 442. The single transferred gene may preferably be a dominant or recessive allele. Preferably, the single transferred gene will confer such trait as male sterility, herbicide resistance, insect resistance, resistance for bacterial, fungal, or viral disease, male fertility, improved harvest characteristics, enhanced nutritional quality and enhanced sugar content. The single gene may be a naturally occurring cantaloupe gene or a transgene introduced through genetic engineering techniques.

The invention further provides methods for developing cantaloupe plant in a cantaloupe plant breeding program using plant breeding technique including recurrent selection, backcrossing, pedigree breeding, restriction fragment length polymorphism enhanced selection, genetic marker enhanced selection and transformation. In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites. Many of them have been discovered and used in melon, see Danin Poleg et al., Cucurbit Genet. Coop Rpt. 21:25–28 (1998) and Kovalski et al., G. E. Lester and J. R. Dunlap (eds.) p191–195 (1995). The first maps using molecular markers have been published in 1996 (Baudracco et al, Theor. Appl. Genet. 93:57–64) and in 1997 (Wang et al, Theor. Appl. Genet. 95:791–797). At the time they were not saturated and few horticultural traits have been placed, but since, Perin et al. Cucurbitaceae (1998:370–376) constructed a Genetic Map of melon with molecular markers (AFLP and SSR) and horticultural traits: *fusarium* wilt resistance (gene Fom-1 and Fom-2), *aphis gossypii* resistance (gene Vat), melon necrotic spot virus resistance (gene nvs), five carpels (gene p) green flesh color (gene gf), various fruit characters (sugars, organic acids, etc.). These markers may be advantageously used for breeding in Marker Assisted Selection as it can be seen in Zheng et al., Theor. Appl. Genet. 99:453–463 where PCR based CAPS (cleaved amplified polymorphic sequences) are used as markers linked to resistance/susceptibility for *Fusarium* wilt in melon. Seeds, cantaloupe plant, and parties thereof produced by such breeding methods are also part of the invention.

DEFINITIONS

In the description and tables that follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Cavity. As used herein, cavity refers to the center of the cantaloupe fruit containing seeds and maternal tissues.

Doradia. Doradia is a physiological vine disorder occurring in Northern and Central Mexico. It includes a yellowing of the plant followed by eventual vine wilt and collapse. It is not pathogenic. Varieties differ in their degree of susceptibility/tolerance to this.

Essentially all the physiological and morphological characteristics. A plant having essentially all the physiological and morphological characteristics means a plant having the physiological and morphological characteristics, except for the characteristics derived from the converted gene.

Yield. Yield defined as concentrated, semi concentrated or extended. Concentrated=Harvested quantity of yield in x consecutive days of harvest. Semi concentrated=Harvested quantity in x+3–5 consecutive days. Extended=Harvested quantity in x+6–10 days. The harvest may also be defined accordingly to the same criteria, i.e. concentrated, when the plant sets all its fruits in a short period of time, semi concentrated and extended, when the plant sets all its fruits and allows a picking in a long period of time.

Firm fruit exterior. Fruit Firmness subjectively tested under field conditions for resistance of fruit exterior against a given pressure. Range is soft, medium, firm and very firm Season maturity. Maturity is considered the date of the onset of harvest and is Very Early, Early, Mid Early, Main and Late Flesh color. Flesh color defined as degree of intensity of orange. Range is pale, medium, medium dark, and deep Coarse netting. The height and density of the netting (reticulation) that covers orange flesh melons. Range is fine, medium, medium coarse and coarse. (i.e.—a fine net would be low and would have noticeable space between the net, a coarse net would be quite high and almost completely cover the fruit exterior. Ideal net is medium or medium coarse Number of Boxes per Acre. The Number of Boxes per Acre—6's, 9's, 12's, 15's, 18's or 23's refers to the number of fruit that fit into a standard cantaloupe box.

Quantitative Trait Loci (QTL) Quantitative trait loci refer to genetic loci that control to some degree numerically representable traits that are usually continuously distributed.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Slight round oval shape. Refers to external fruit shape. Range is Flat Round, Round, round oval, oval, elongate.

Abscission zone. This is the zone of abscission or separation of the fruit from the peduncle at maturity (controlled by ethylene). The resulting zone (or scar) ranges in size, small being preferred over large—range small (<10 mm), medium (10–15 mm), large (15–20 mm), very large (>20 mm)

Blossom scar. This is the remnant scar from the stigmatic surface of the blossom. There is a very broad range in sizes, small is better. Range is small (<10 mm), medium (10–20 mm), large (20–40 mm) and very large (>40 mm)

Fruit size. Western Shipper fruit size determined two ways 1/. Range in kilograms: small (below 1.5), medium (1.5–1.8), large (1.8–2.2), very large (above 2.2) 2/. # Fruit that fit into a standard western melon packing box: 6, 9, 12, 15, 18, 23, 30. Small: some 18's, 23's, 30's, Medium: some 12's, 15's 18's, Large: 9's, 12's, few 15's and Extra Large: few 6's, 9's few 12's.

Soluble Solids. Soluble solids refer to the percent of solid material found in the fruit tissue, the vast majority of which is sugars. Soluble solids are estimated with a refractometer and measured as degrees Brix. Soluble Solids vary with environment. For example, for California summer growing conditions the following range would apply. Very high (>12.5%), high (11.5–12.5%), medium (10.5–11.5%), low <10.5%)

Flesh firmness. Flesh firmness subjectively tested under field conditions for resistance of flesh against a given pressure. Range is soft, medium, firm or very firm.

DETAILED DESCRIPTION OF THE INVENTION

Inbred cantaloupe line 442 is an andromonoecious western shipper cantaloupe with superior characteristics, and provides an excellent parental line in crosses for producing first generation ($F_1$) hybrid cantaloupe. Inbred cantaloupe line 442 is best adapted to southern and southwestern regions of the USA as well as Latin America. Inbred cantaloupe line 442 produces small fruit size with round shape, small abscission zone, very small cavity, medium coarse netting and small blossom scar. The yield is very high, with an extended harvest profile. The level of soluble solids is very high. The vine is very vigorous with excellent fruit coverage and a very dark green color. Inbred cantaloupe line 442 is also tolerant to races 1 and 2 of *spaerotheca fuliginea* (Powdery Mildew) and to "doradia", a physiological vine yellowing disorder found in parts of Mexico. Inbred 442 also has tolerance to sulfur applications. Inbred 442 can be used to produce main season maturity hybrid cantaloupe varieties having an extended yield, with medium fruit size having very firm flesh, a slight round oval shape, a firm exterior, a medium net, a medium dark flesh color and tolerant to races 1 and 2 of *spaerotheca fuliginea* and "doradia".

Inbred cantaloupe line 442 has superior characteristics and was developed from the F1 cross 4678*45599, which was made 1978 in the greenhouse at Harris Moran Research Station in Davis, Calif. The $F_2$ were grown in Davis, Calif. in 81, with a selection based horticultural criteria (plot 81 D69 O.P.). $F_3$ selection, plot number 83D126 O.P, was made at Davis, Calif. in 1983. The $F_4$ selections were made in 1984 in Davis Calif., in greenhouses and the disease pressure selection began. $F_5$ plants were selected in a field plot in California in 1987, $F_6$ selections were made in 1989 in Davis, Calif. $F_7$ generation was selected in 1991 in Davis, Calif. $F_8$ plants were selected in Davis, Calif. during 1994. $F_9$ plants were selected in 95, $F_{10}$ plants in 97. In 1999, the plants surviving powdery mildew were selected in greenhouses. Plants were again selected for horticultural criteria in 2000 and in 2001. Selection pressure was for high yield, fruit type uniformity, high soluble solids, dark orange internal color, small to medium fruit size and round shape, strong net, firm flesh, normal abscission profile as well as tolerance to *spaerotheca fuliginea* and sulfur applications. Surprisingly, Inbred 442 has been found also tolerant to Doradia.

Inbred 442 is similar to the standard open pollinated cultivar 'Topmark'. Topmark' is a full netted western shipping type cantaloupe. While similar to inbred 442, 'Topmark' has numerous differences including: Inbred 442 matures at least 3–4 days earlier than 'Topmark". 'Topmark' is variable for it's fruit size distribution, where inbred 442 has a very uniform fruit size profile. 'Topmark' has irregular fruit shape, including a tendency to have triangulate fruit; inbred 442 has a very regular shape. Inbred 442 has intermediate tolerance to downy mildew where 'Topmark' is extremely susceptible. Inbred 442 is tolerant to Doradia while 'Topmark' is susceptible.

During the development of the line, crosses were made to inbred testers for the purpose of estimating the line's general and specific combining ability, and parallel evaluations were run in the USA by the Davis, Calif. Research Station. The inbred was evaluated further as a line and in numerous crosses by Davis, Calif. Research station. The inbred has proven to have a good combining ability in hybrid combinations.

The inbred line has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred 442.

Inbred cantaloupe line 442 has the following morphologic and other characteristics (based primarily on data collected at Davis, Calif.).

Variety Description Information

PLANT TYPE: Andromonoecious
REGION WHERE DEVELOPED: California
AREA OF BEST ADAPTATION IN THE USA: California, Arizona
MATURITY: 84–91 Days
Number of days earlier than TopMark: 2
LEAF (MATURE BLADE OF THIRD LEAF):
Shape: ovate
shallowly lobed
dark green
Length: 57 mm
Width: 49 mm
Surface: pubescent
FRUIT (at edible maturity):
Length: 129 cm
Diameter: 127 cm
Weight: 1200 gm
Shape: round,
Surface: netted,
Blossom scar: obscure
Ribs: present
Number of ribs per fruit: 8
Rib width at medial: 5 mm
Sutures: shallow, netted
Shipping quality: excellent
Fruit abscise: when ripe
RIND NET:
abundant
Distribution: covers entire fruit
Coarseness: medium coarse
Interlacing: complete
Interstices: medium deep
RIND TEXTURE:
firm
thickness at medial: 6 mm
RIND COLOR (AT EDIBLE MATURITY):
Primary color: buff
Net color: grayish tan
Mottling color: none
Furrow (suture) color: green
RIND COLOR (AT FULL MATURITY):
Primary color: creamy yellow
Net color: tan
Mottling color: none
Furrow (suture) color: light yellow
FLESH (AT EDIBLE MATURITY):
Color near cavity: dark orange
Color in center: dark orange
Color near rind: green
Refractometer percentage of soluble solids: 11.9%
As compared to (Topmark) 12.6%
Aroma: faint
Flavor: somewhat spicy
SEED CAVITY:
Length: 52 mm
Width: 52 mm
Shape in x-section: circular
SEEDS:
Number of seeds per fruit: 284
Weight of 1000 seeds: 28.2 gm
DISEASE RESISTANCE Rating (1=susceptible–5=resistant)
Bacterial wilt: 1
Powdery mildew: 4
Watermelon mosaic: 1
Anthracnose: 1
Root rot: 1
Verticillum wilt: 4
Downy mildew: 3
Cucumber mosaic: 1
*Fusarium* wilt: 1
Melon rust: 1
Other: Doradia: 4

Further Embodiments of the Invention

This invention also is directed to methods for producing a cantaloupe plant by crossing a first parent cantaloupe plant with a second parent cantaloupe plant wherein either the first or second parent cantaloupe plant is an inbred cantaloupe plant of the line 442. Further, both first and second parent cantaloupe plants can come from the inbred cantaloupe line 442. Still further, this invention also is directed to methods for producing an inbred cantaloupe line 442-derived cantaloupe plant by crossing inbred cantaloupe line 442 with a second cantaloupe plant and growing the progeny seed, and repeating the crossing and growing steps with the inbred cantaloupe line 442-derived plant from 0 to 7 times. Thus, any such methods using the inbred cantaloupe line 442 are part of this invention: selfing, backcrosses, hybrid production, crosses to populations, and the like. All plants produced using inbred cantaloupe line 442 as a parent are within the scope of this invention, including plants derived from inbred cantaloupe line 442. Advantageously, the inbred cantaloupe line is used in crosses with other, different, cantaloupe inbreds to produce first generation ($F_1$) cantaloupe hybrid seeds and plants with superior characteristics.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which cantaloupe plants can be regenerated, plant calli, plant clumps and plant cells that are intact in plants or parts of plants, such as embryos, pollen, ovules, flowers, leaves, stalks, and the like.

As it is well known in the art, tissue culture of cantaloupe can be used for the in vitro regeneration of cantaloupe plants. Tissues cultures of various tissues of cantaloupe and regeneration of plants therefrom are well known and published. By way of example, a tissue culture comprising organs has been used to produce regenerated plants as described in Dirks R., et al. *Plant Cell Report* 7: 8 626–627 (1989); Tahar, S. B., et al. *Cucurbit Genetics Cooperative Reports* 12:21–27 (1989); Homma, Y., et al. *Japan J. Breed* 41:543–551 (1991). Yoshioka, K., et al. *Japan J Breed* 42:277–285 (1992); Debeaujon, I., et al. *Pl Cell Rep* 12:37–40 (1992); Tabei, Y., et al. *J Jap Soc Hort Sci* 61:317–322 (1992); Debeaujon, I., et al. *Plant Cell Tissue Org Cult* 34:91–100 (1993); Fang, G. W., et al. *Molecular Plant—Microbe Interactions* 6:358–367 (1993); Valles, M. P., et al. *Pl Cell Rep* 13:145–148 (1994); Ezura, H., et al. *Pl Cell Rep* 14:107–111 (1994); Ezura, H., et al. *Pl Cell Rep* 14:684–688 (1995); Kathal, R., et al. *Plant Sci* 96:137–142 (1994); Adelberg, J. W., et al. *Hortscience* 29:689–692 (1994). More precisely, in the case of the melon (*C. melo*), regeneration through organogenesis has been described either directly on cotyledons placed in culture, Smith, S. et al., *Abstract Proc. Annual TCA Meeting*, Las Vegas, Nev., (1988). Dirks, R. et al., *Plant Cell Reports*, 7:626–627 (1989), or through the intermediary of calli derived from cotyledons, Mackay, W. et al., *Cucurbit Genetics Cooperative*, 11:33–34 (1988), Moreno, V. et al., *Plant Cell Tissue and Organ Culture*, 5:139–146 (1985), Orts, M. et al., *Hort Science*, 22:666 (1987), Bouabdalla, L. et al., *Z. Pflanzenz chtung*, 96:82–85 (1986), hypocotyls, Abak, K. et al., *Cucurbit Genetics Cooperative Report*, 3:27–29 (1980), Kathal, R. et al., *J. Plant Physiol.*, 126:59–62 (1986) or leaves, Kathal, R. et al., *Plant Cell Report*, 7:449–451 (1988). The production of melon plants derived from somatic embryos has also been reported, Oridate, T. et al., *Japan J. Breeding*, 36:424–428 (1986), Branchard, M. et al., *C.R. Acad. Sci.* Paris, 307, S rie III:777–780 (1988). Also, De Both et al. in U.S. Pat. No. 6,198,022 teach how to regenerate plants having a normal phenotype from cotyledons. It is clear from the literature that the state of the art is such that these methods of obtaining plants are, and were, "conventional" in the sense that they are routinely used and have a very high rate of success. Thus, another aspect of this invention is to provide cells which upon growth and differentiation produce cantaloupe plants having the physiological and morphological characteristics of inbred cantaloupe line 442.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed cantaloupe plants, using transformation methods as described below to incorporate transgenes into the genetic material of the cantaloupe plant(s).

Expression Vectors for Cantaloupe Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983), Valles et al., *Plant Cell Report*, 13:3–4 145–148 (1994), Fang et al., *Plant Cell Report*, 9:3 160–164 (1990). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990< Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) Stalker et al., *Science* 242:419–423 (1988) and Qui Zhijun et al., *International Journal of Horticultural Science* 5:3/4 46–49 (1999).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include Beta-glucuronidase (GUS),alpha-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), Valles et al, *Plant Cell Report* 3:3–4 145–148 (1994), Shetty et al., *Food Biotechnology* 11:2 111–128 (1997).

Recently, in vivo methods for visualizing GUS activity that do not require destruction of plant tissue have been made available. Molecular Probes publication 2908, Imagene Green™, p. 1–4 (1993) and Naleway et al.,*J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in cantaloupe. Optionally, the inducible promoter is operably linked to a nucleotide sequence encoding a signal sequence which is operably linked to a gene for expression in cantaloupe. With an inducible promoter the rate of transcription increases in response to an inducing agent.

Any inducible promoter can be used in the instant invention. See Ward et al., *Plant Mol. Biol.* 22:361–366 (1993).

Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) Tet repressor from Tn10 (Gatz et al., *Mol. Gen. Genetics* 227:229–237 (1991) or the salicylic acid inducible promoter region of the protein gene PR1 from tobacco as described in Shetty et al., *Food Biotechnology* 11:2 111–128 (1997). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in cantaloupe or the constitutive promoter is operably linked to a nucleotide sequence encoding a signal sequence which is operably linked to a gene for expression in cantaloupe.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985), Dong et al., *Biotechnology* 9:9 858–863 (1991) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/Ncol fragment 5' to the *Brassica napus* ALS3 structural gene (or a nucleotide sequence similarity to said Xba1/Ncol fragment), represents a particularly useful constitutive promoter. See PCT application WO96/30530.

C. Tissue-Specific or Tissue-Preferred Promoters

A tissue-specific promoter is operably linked to a gene for expression in cantaloupe. Optionally, the tissue-specific promoter is operably linked to a nucleotide sequence encoding a signal sequence which is operably linked to a gene for expression in cantaloupe. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is cantaloupe. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press, Boca Raton* 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt ȧ-endotoxin gene. Moreover, DNA molecules encoding a-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., *Plant Molec. Biol.* 24:25 (1994), who disclose the nucleotide sequences of several *Clivia miniata* mannose-binding lectin genes.

D. A gene coding for the coat protein of the cucumber mosaic virus (CMV), see Gonzalves et al., *Journal of the American Society for Horticultural Science.* 1994, 119: 2, 345–355.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* ȧ-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-â, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo ȧ-1,4-D-polygalacturonases facilitate fungal colonization and plant nutrient release by solubilizing plant cell wall homo-ȧ-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A development-arrestive protein produced in nature by a plant. For example, Logemann et al., *Bioi/Technology* 10:305 (1992), have shown that transgenic plants expressing the barley ribosome-inactivating gene have an increased resistance to fungal disease.

S. A gene of the Zucchini Yellow Mosaic Potyvirus (ZYMV) coat protein that, when introduced into melon by

*Agrobacterium tumefaciens* mediated transformation, seems to render the transformed melon immune to infection by ZYMV. See for example Fang et al., *Molecular Plant Microbe Interaction.* 1993, 6:3, 358–367.

2. Genes that Confer Resistance to a Herbicide, For Example:

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+ genes) and a benzonitrile (nitrilase gene). Przibilla et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:

A. Increased sweetness and flavor of the fruit by introduction of a gene encoding sweet testing proteins such as monellin, see for example Penarrubia et al., *BioTechnology.* 1992,10:5, 561–564 or thaumatin, see Szwack et al., *Proceedings of the IXth International Congress of the International Association of Plant Tissue Culture and Biotechnology*, Jerusalem, Israel, 14–19 Jun. 1998.

B. Reduced ethylene biosynthesis to control ripening by introduction of a antisens construct of the ACC oxidase into *cucumis melo*. For example, see Guis et al., *Proceedings if the eighth International Symposium on Plant Bioregulators in Fruit Production*, Val. Spain, 1–4 Apr. 1997.

C. Improved salt tolerance by transforming *Cucumis melo* plant with HAL 1, a yeast regulatory gene involved in stress tolerance, as shown in Serrano et al., *Scientia Horticuturae.* 1999, 78:1/4 , 261–269 or in Bordas et al., *Transgenic Research.* 1997, 6: 1,41–50.

D. Obtained male sterile plants, especially useful in hybrid melon production, by introduction of a gene encoding a tobacco PR Glucanase as described in tomato (WO9738116) but that can also be used in melon.

Methods for Cantaloupe Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. *Agrobacterium*-Mediated Transformation

One method for introducing an expression vector into plants is based on the natural transformation system of *Agrobacterium*. See, for example, Horsch et al., *Science* 227:1229 (1985). Guis et al., *Scientia Horticulturae.* 2000, 84:1/2, 91–99, Ann et al., *Embo J.* 277–284:4, (1985), Jefferson et al., *Embo J.* 3901–390764, (1987), Valles et al., *Pl Cell. Rep.* 145–148:13 (1984). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 6,198,022 issued Mar. 6, 2001.

B. Direct Gene Transfer

Despite the fact the host range for *Agrobacterium*-mediated transformation is broad, some major cereal crop or vegetable species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 im. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992), Gonzalves et al., *Journal of the American Society for Horticultural Science.* 1994, 119: 2, 345–355, Gray et al., *Plant Cell Tissue and Organ Culture.* 1994, 37:2,179–184.

Another method for physical delivery of DNA to plants is sonication of target cells. Zhang et al., *Bio/Technology* 9:996 (1991). Alternatively, liposome or spheroplast fusion have been used to introduce expression vectors into plants.

Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of V11th International Congress on Plant Cell and Tissue Culture IAPTC, A2–38, p 53 (1990); D'Halluin et al., *Plant Cell* 4:1495–1505 (1992), Spencer et al., *Plant Mol. Biol.* 24:51–61 (1994) and Nishigughi et al., *Bulletin of the National Institute of Agrobiological Resources Japan.* 1988, 4,177–187.

Following transformation of cantaloupe target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular cantaloupe line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred cantaloupe plant is used in the context of the present invention, this also includes any single gene conversions of that inbred. The term single gene converted plant as used herein refers to those cantaloupe plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental cantaloupe plants for that inbred. The parental cantaloupe plant which contributes the gene for the desired characteristic is termed the nonrecurrent or donor parent. This terminology refers to the fact that the nonrecurrent parent is used one time in the backcross protocol and therefore does not recur. The parental cantaloupe plant to which the gene or genes from the nonrecurrent parent are transferred is known as the recurrent parent as it is used for several rounds in the backcrossing protocol (Poehiman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a cantaloupe plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility (such as a PR glucanase gene), herbicide resistance, resistance for bacterial, fungal (genes Fom-1 and Fom-2 for resistance to *fusarium* wilt), or viral disease (gene nvs for resistance to melon necrotic spot virus), insect resistance (gene Vat for resistance to *aphis gossypii*), male fertility, enhanced nutritional quality, enhanced sugar content, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Tables

In the tables that follow, the traits and characteristics of inbred cantaloupe 442 are given compared to other inbreds. The data collected are presented for key characteristics and traits. Inbred 442 was tested as an inbred, but also in several hybrid combinations at numerous locations, with two or three replications per location. Information about these inbreds and hybrids, as compared to several check inbred and hybrids is presented Table 1: Inbred characteristics The inbred name is shown in column 1

The fruit weight (Wt.) in Kilograms is shown in column 2.

The content in soluble solids in brix is shown in column 3.

The fruit diameter in centimeters is shown in column 4.

The fruit length in centimeters is shown in column 5.
The ratio Length/diameter is shown in column 6.

TABLE 1

Overall Comparisons
Inbred 442 vs. Topmark
Location: 2001 In Davis, CA

| Inbred | WT. | Soluble solids | Fruit diameter | Fruit length | Length/Diameter |
|---|---|---|---|---|---|
| Inbred 442 | 1.20 | 11.89 | 12.72 | 12.88 | 1.01 |
| TopMark | 1.25 | 12.65 | 12.95 | 13.54 | 1.04 |

Table 2: Inbred characteristics
The inbred name is shown in column 1
The cavity (cm) is shown in column 2.
The cavity to diameter ratio is shown in column 3.
The early Harvest number (number of fruit out of 30 total harvested by a given date) is shown in column 4.
The late Harvest number (number of fruit out of 30 total harvested after a given date) is shown in column 5
The presence/absence of sutures is shown in column 6.

TABLE 2

Overall Comparisons
Inbred 442 vs. Topmark
Location: 2001 In Davis, CA

| Inbred | Cavity | Cavity to Diameter Ratio | Early Harvest | Late Harvest | Sutures |
|---|---|---|---|---|---|
| Inbred 442 | 5.27 | 2.47 | 15 | 15 | Present |
| TopMark | 5.68 | 2.40 | 2 | 28 | Absent |

Table 3: Inbred characteristics: Powdery Mildew Race 2
The inbred name is shown in column 1
The seed source used is shown in column 2.
The reaction of each line to Powdery Mildew race 2 is shown in column 3. T indicates a tolerant reaction to the pathogen. S indicates a susceptible reaction to the pathogen.
The number of Healthy (H) plant and the number of lightly symptomatic (L) plant is shown in column 4. The total number of plant tested is also indicated in column 4. For example, 23H0L/23 means that 23 plants are healthy, none are lightly symptomatic and 23 were tested.

TABLE 3

Overall Comparisons
Inbred 442 vs. Topmark
Location: 2001 In Davis, CA

| Inbred | Lot | Powdery Mildew race 2 Reaction | Healthy and/or susceptible plants |
|---|---|---|---|
| Inbred 442 | 00-2109 | T | 23H 0L/23 |
| Inbred 442 | 00-2110 | T | 21H 0L/21 |
| Inbred 442 | 0003314-1 | T | 24H 0L/24 |
| Inbred 442 | 0003314-2 | T | 22H 1L/23 |
| Inbred 442 | 0003314-3 | T | 24H 0L/24 |
| Inbred 442 | 0003314-4 | T | 24H 0L/24 |
| Inbred 442 | 0003314-5 | T | 24H 0L/24 |
| Topmark | 85-1077 | S | 0H/24 |

Table 4 and 5: Hybrid Comparisons
The hybrid name/formula is shown in column 1
The weight in Kilograms is shown in column 2.
The exterior color is shown in column 3. Subjective Ratings 1=very poor (non marketable) 3=poor (non marketable) 5=average (marketable) 7=very good (much better than industry standards) 9=superior (further improvement not attainable).

The exterior firm is shown in column 4. Subjective Ratings 1=very poor (non marketable), 3=poor (non marketable), 5=average (marketable) 7=very good (much better than industry standards), 9=superior (further improvement not attainable)

The surface decay is shown in column 5. Subjective Ratings 1=very poor (non marketable), 3=poor (non marketable), 5=average (marketable) 7=very good (much better than industry standards), 9=superior (further improvement not attainable)

The Interior color is shown in column 6. Subjective Ratings 1=very poor (non marketable), 3=poor (non marketable), 5=average (marketable) 7=very good (much better than industry standards), 9=superior (further improvement not attainable)

The rind is shown in column 7. Subjective Ratings 1=very poor (non marketable), 3=poor (non marketable), 5=average (marketable) 7=very good (much better than industry standards), 9=superior (further improvement not attainable)

The soluble solids in brix is shown in column 8.
The cut flesh firmness measured in lbs resistance per sq inch is shown in column 9

TABLE 4

Overall Comparisons
Hybrid vs. Check Hybrids
Location: 2001 In Davis, Ca

| Variety | Weight | Exterior color | Exterior Firm | Surface decay | Interior color | Rind | Brix | Cut Flesh |
|---|---|---|---|---|---|---|---|---|
| E69T9* Inbred442 | 1.60 | 6.08 | 6.42 | 5.88 | 6.13 | 6.23 | 11.53 | 3.33 |
| Inbred441* Inbred442 | 1.83 | 5.33 | 5.94 | 6.19 | 5.78 | 5.69 | 11.90 | 3.54 |
| Hymark | 1.85 | 5.73 | 6.03 | 5.87 | 6.07 | 5.76 | 12.01 | 3.16 |
| Oro Rico | 1.45 | 6.58 | 6.37 | 6.65 | 6.47 | 6.00 | 13.17 | 2.95 |
| Grand Total | 1.78 | 5.78 | 6.00 | 5.99 | 5.95 | 5.91 | 12.12 | 3.05 |

TABLE 5

Overall Comparisons
Hybrid vs. Check Hybrids
Location: 2000 In Davis, Ca

| Variety | Weight | Exterior color | Exterior Firm | Surface decay | Interior color | Rind | Brix | Cut Flesh |
|---|---|---|---|---|---|---|---|---|
| Mission | 1.53 | 6.52 | 6.90 | 6.86 | — | — | 13.18 | 3.12 |
| E69T9* Inbred442 | 1.75 | 5.85 | 7.00 | 6.28 | — | — | 11.60 | 4.01 |
| Oro Rico | 1.49 | 6.35 | 6.45 | 6.48 | — | — | 13.18 | 3.29 |
| Hymark | 1.62 | 5.75 | 6.50 | 6.23 | — | — | 12.52 | 3.33 |

Table 6: Hybrid Comparisons
The hybrid name/formula is shown in column 1
The total yield in carton per acre (Y) is shown in column 2
The percentage of early harvest (date ranges indicating harvest profiles for maturity determinations) is shown in column 3.
The percentage of mid-early harvest (date ranges indicating harvest profiles for maturity determinations) is shown in column 4.
The percentage of late Harvest (date ranges indicating harvest profiles for maturity determinations) is shown in column 5.
The percentage of 9's, 12's, 15's, 18's, 23's melons is shown in columns 6, 7, 8, 9 and 10 respectively
The percentage of culls (fruit which are determined not to be marketable for various reasons) is shown in column 11
The brix average (B) is shown in column 12

TABLE 6

Overall Comparisons
Hybrid vs. Check Hybrids
Location: 2001 in California

| Variety | Y | % early harvest | % mid early harvest | % late harvest | % 9's | % 12's | % 15's | % 18's | % 23's | % culls | B |
|---|---|---|---|---|---|---|---|---|---|---|---|
| E69T9*Inbred442 | 1340 | 80 | 30 | 10 | 2.6 | 20.2 | 39 | 25.7 | 11.2 | 1.4 | 9.7 |
| Oro Rico | 1226 | 68 | 23 | 9 | 1.8 | 12 | 42.4 | 26.3 | 13 | 4.5 | 9.2 |
| Hymark | 1232 | 50 | 46 | 4 | 0.8 | 7.8 | 42.3 | 35.3 | 11.6 | 2.3 | 10.2 |
| Mission | 1201 | 50 | 43 | 7 | 0.2 | 6.4 | 40.6 | 33 | 16.1 | 3.8 | 10.6 |

Table 7: Hybrid Comparisons

The hybrid name/formula is shown in column 1

The yield rating (Y) is shown in column 2. Subjective Ratings 1=very poor (non marketable), 3=poor (non marketable), 5=average (marketable) 7=very good (much better than industry standards), 9=superior (further improvement not attainable)

The yield as concentrate, semi or extended is shown in column 3.

The maturity is shown in column 4.

The shape is shown in column 5.

The firmness is shown in columns 6. Subjective Ratings 1=very poor (non marketable), 3=poor (non marketable), 5=average (marketable) 7=very good (much better than industry standards), 9=superior (further improvement not attainable)

The flesh texture is shown in column 7.

The color is shown in column 8. Subjective Ratings 1=very poor (non marketable), 3=poor (non marketable), 5=average (marketable) 7=very good (much better than industry standards), 9=superior (further improvement not attainable)

The cavity size is shown in column 9. Subjective Ratings 1=very poor (non marketable), 3=poor (non marketable), 5=average (marketable) 7=very good (much better than industry standards), 9=superior (further improvement not attainable).

The percentage of 9's, 12's, 15's, 18's, 23's melons is shown in columns 10,11,12, 13 and 14 respectively The average brix is shown in column 15.

TABLE 7

Part a) Columns 1–8
Overall Comparisons
Hybrid vs. Check Hybrids
Location: 2000–2001 in California

| Variety | YIELD | CONC SET | MATURITY | SHAPE | FIRMNESS | FLESH TEXTURE | COLOR |
|---|---|---|---|---|---|---|---|
| E69T9*Inbred442 | 5.30 | EXTENDED | MID SEASON | ROUND OVAL | 6.10 | VERY FIRM | 5.85 |
| Inbred 441*Inbred442 | 5.9 | SEMI CONCENTRATED | MID EARLY | SLIGHT OVAL | 6.6 | VERY FIRM | 5.7 |
| Hymark | 5.25 | SEMI CONCENTRATED | MID SEASON | SLIGHT OVAL | 6.55 | FIRM | 6.30 |
| Oro Rico | 6.1 | EXTENDED | MID SEASON | ROUND | 6.8 | VERY FIRM | 6.45 |

TABLE 7

Part b) Columns 1, 9–14
Overall Comparisons
Hybrid vs. Check Hybrids
Location: 2000–2001 in California

| Variety | CAVITY | SIZE-9 | SIZE-12 | SIZE-15 | SIZE-18 | SIZE-23 | BRIX |
|---|---|---|---|---|---|---|---|
| E69T9*Inbred442 | 5.90 | 20% | 35% | 35% | 10% | 0% | 12.42 |
| Hymark | 5.3 | 35% | 40% | 20% | 5% | 0% | 10.3 |
| Hymark | 5.40 | 0% | 25% | 50% | 15% | 10% | 11.99 |
| Oro Rico | 5.15 | 5% | 35% | 35% | 20% | 5% | 12.03 |

Deposit Information

Deposits of the Harris Moran Seed Company proprietary inbred cantaloupe line 442 and the cantaloupe hybrid E69T9*Inbred 442 disclosed above and recited in the appended claims have been made with National Collections of Industrial Food and Marine Bacteria (NCIMB), 23 St. Machar Drive, Aberdeen, Scotland, AB24 3RY, United Kingdom. The date of deposit was Jan. 5, 2005. The deposits of 2,500 seeds each were taken from the same deposits maintained by Harris Moran Seed Company since prior to the filing date of this application. All restrictions upon the deposits have been removed, and the deposits are intended to meet all of the requirements of 37 C.F.R. §1.801–1.809. The NCIMB accession number for inbred cantaloupe line 442 is NCIMB 41264. The NCIMB accession number for cantaloupe hybrid E69T9*Inbred 442 is NCIMB 41265. The deposits will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. An inbred cantaloupe seed designated Inbred 442 wherein a sample of said seed has been deposited under NCIMB 41264.

2. A cantaloupe plant, or part thereof, produced by growing the seed of claim 1.

3. Pollen of the plant of claim 2.

4. An ovule of the plant of claim 2.

5. A cantaloupe plant, or a part thereof, having all of the physiological and morphological characteristics of the cantaloupe plant of claim 2.

6. A tissue culture of regenerable cells of a cantaloupe plant of claim 2, wherein the tissue regenerates plants having all the morphological and physiological characteristics of inbred cantaloupe line 442, representative seeds having been deposited under NCIMB 41264.

7. The tissue culture of claim 6, wherein the cells are from a plant part selected from the group consisting of embryos, protoplast, meristematic cells, callus, pollen, leaves, anthers, stems, petioles, roots, root tips, fruits, seeds, flowers, cotyledons and hypocotyls.

8. A cantaloupe plant regenerated from the tissue culture of claim 6, wherein the plant expresses all the morphological and physiological characteristics of inbred cantaloupe line 442, representative seeds having been deposited under NCIMB 41264.

9. A method for producing a hybrid cantaloupe seed, wherein the method comprises crossing a first inbred parent cantaloupe plant with a second inbred parent cantaloupe plant to produce a hybrid cantaloupe seed and harvesting the hybrid cantaloupe seed, wherein said first or second inbred parent cantaloupe plant is the cantaloupe plant of claim 2.

10. A method of producing a transgenic cantaloupe plant, wherein the method comprises transforming the cantaloupe plant of claim 2 with a transgene wherein the transgene confers a characteristic selected from the group consisting of herbicide resistance, insect resistance, resistance to bacterial disease, resistance to fungal disease, resistance to viral disease, male sterility, increased sweetness, increased flavor, improved ripening control and improved salt tolerance.

11. A transgenic cantaloupe plant produced by the method of claim 10.

12. A method of producing an herbicide resistant cantaloupe plant, wherein the method comprises transforming the cantaloupe plant of claim 2 with a transgene that confers herbicide resistance.

13. An herbicide resistant cantaloupe plant produced by the method of claim 12.

14. A method of producing an insect resistant cantaloupe plant, wherein the method comprises transforming the cantaloupe plant of claim 2 with a transgene that confers insect resistance.

15. An insect resistant cantaloupe plant produced by the method of claim 14.

16. A method of producing a disease resistant cantaloupe plant, wherein the method comprises transforming the cantaloupe plant of claim 2 with a transgene that confers resistance to bacterial, fungal or viral disease.

17. A disease resistant cantaloupe plant produced by the method of claim 16.

18. A method of producing a male sterile cantaloupe plant, wherein the method comprises transforming the cantaloupe plant of claim 2 with a transgene that confers male sterility.

19. A male sterile cantaloupe plant produced by the method of claim 18.

20. A method of producing a cantaloupe plant which produces fruits with increased sweetness and flavor, wherein the method comprises transforming the cantaloupe plant of claim 2 with a transgene that confers increased sweetness and flavor of the fruit.

21. A cantaloupe plant which produces fruits with increased sweetness and flavor, said plant produced by the method of claim 20.

22. A method of producing a cantaloupe plant with improved ripening control, wherein the method comprises transforming the cantaloupe plant of claim 2 with a transgene that confers improved ripening control.

23. A cantaloupe plant with improved ripening control produced by the method of claim 22.

24. A method of producing a cantaloupe plant with improved salt tolerance, wherein the method comprises transforming the cantaloupe plant of claim 2 with a transgene that confers improved salt tolerance.

25. A cantaloupe plant with improved salt tolerance produced by the method of claim 24.

26. A hybrid cantaloupe seed designated E69T9*Inbred 442 having inbred line 442 as a parental line, representative seed of said hybrid having deposited under NCIMB 41265.

27. A hybrid cantaloupe plant produced by growing the hybrid seed of claim 26.

* * * * *